US00PP20477P3

(12) United States Plant Patent
White

(10) Patent No.: US PP20,477 P3
(45) Date of Patent: Nov. 10, 2009

(54) APPLE TREE VARIETY NAMED 'SCILATE'

(50) Latin Name: ***Malus domestica* Borkh.**
Varietal Denomination: Scilate

(75) Inventor: Allan G. White, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/072,658

(22) Filed: Feb. 26, 2008

(65) Prior Publication Data

US 2008/0209602 P1 Aug. 28, 2008

Related U.S. Application Data

(60) Provisional application No. 60/903,999, filed on Feb. 28, 2007.

(51) Int. Cl.
*A01H 5/00* (2006.01)

(52) U.S. Cl. ..... Plt./161

(58) Field of Classification Search ..... Plt./161
See application file for complete search history.

*Primary Examiner*—June Hwu
(74) *Attorney, Agent, or Firm*—Greenlee Winner and Sullivan PC

(57) ABSTRACT

A new and distinct apple tree variety is described. The variety results from selection among a population of seedlings derived from crossing the apple varieties known as 'Royal Gala' (U.S. Plant Pat. No. 4,121) and 'Braeburn' (not patented). The fruit of the apple tree of this new variety has an attractive appearance characterised by its red colour and obvious lenticels and is notable for its excellent eating quality. The new variety has been named 'Scilate'.

7 Drawing Sheets

Genus and species of plant claimed: Species: *Malus domestica* Borkh.

Variety demonimation: 'Scilate'.

BACKGROUND OF THE INVENTION

The new variety was selected from a population of seedlings derived from crossing the apple varieties 'Royal Gala' (female parent, U.S. Plant Pat. No. 4,121) and 'Braeburn' (male parent, not patented). The cross was made in 1985 on trees located on land at Havelock North, Hawkes Bay, New Zealand. The new variety was determined to be distinct from the parent varieties 'Royal Gala' and 'Braeburn', as well as the closely related varieties 'Scifresh' (U.S. Plant Pat. No. 13,888), 'Scigold' (not patented) and 'Sweetie' (not patented), by the following characteristics:

'Royal Gala': 'Scilate' has a later harvest season and firmer flesh.

'Braeburn': 'Scilate' has a later harvest season, fruit with a brighter red colour and obvious lenticels.

'Scifresh': 'Scilate' has a later harvest season, larger fruit lenticels, and larger fruit size.

'Scigold': 'Scilate' has red coloured fruit compared with 'Scigold' which is yellow-green.

'Sweetie': 'Scilate' has a later harvest season, firmer flesh and a more acid flavour.

The variety was first asexually propagated at Havelock North, Hawkes Bay, New Zealand.

The new variety has been named 'Scilate'. Asexual propagation by budding shows that the unique combination of characteristics of the variety come true to form and are established and transmitted through succeeding propagation. In order to obtain true-to-type clones of the initial plant, asexually propagated plants were obtained by budding dormant buds from the original seedling onto MM106 rootstocks.

SUMMARY OF THE INVENTION

The fruit of the apple tree of this new variety has an attractive appearance characterised by its red colour and lenticels and is notable for its excellent eating quality. The new variety has been named 'Scilate'.

BRIEF DESCRIPTION OF PHOTOGRAPHS

The accompanying photographs show typical specimens of the tree, foliage and fruit of the new variety as depicted in colours as nearly true as is reasonably possible to make the same in a colour illustration of this character.

DETAILED BOTANICAL DESCRIPTION

Figure 1:
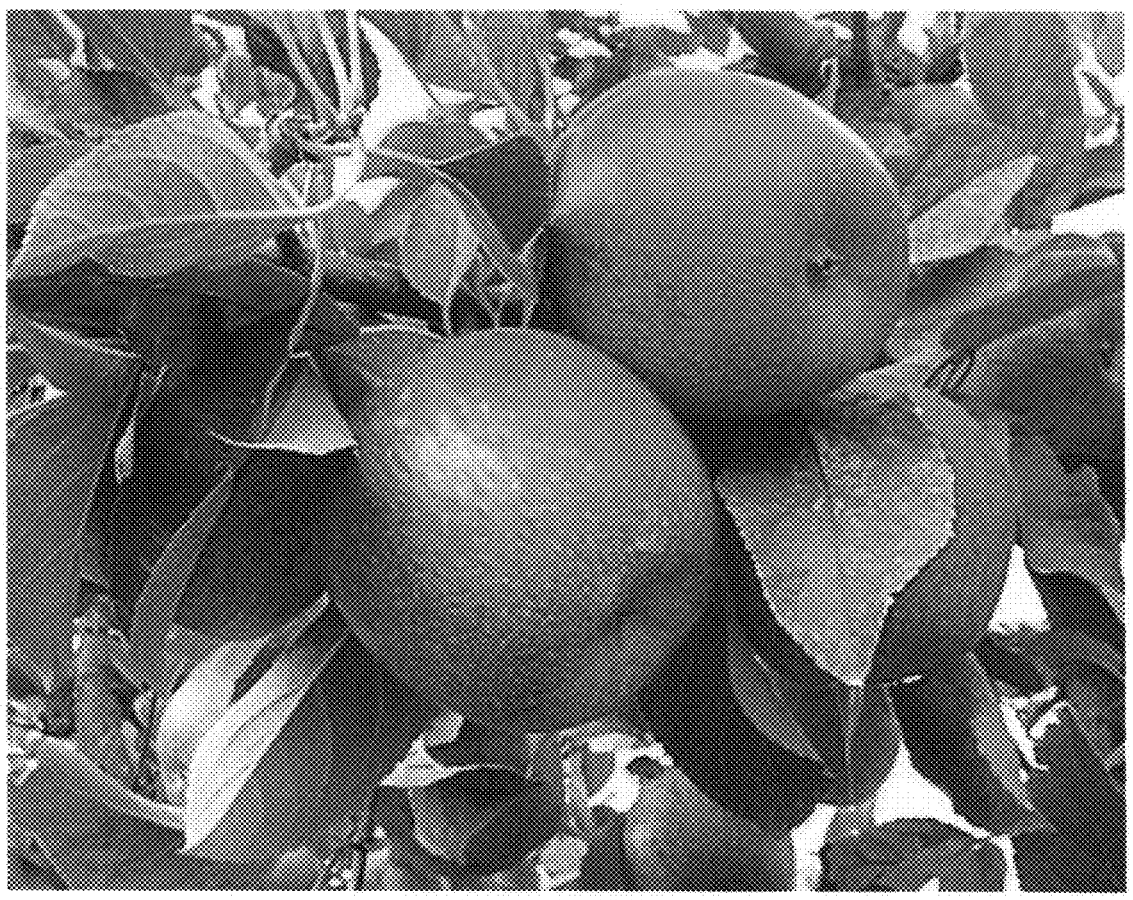
FIG. 1 shows typical fruit of the variety 'Scilate' in the orchard.
Figure 2:
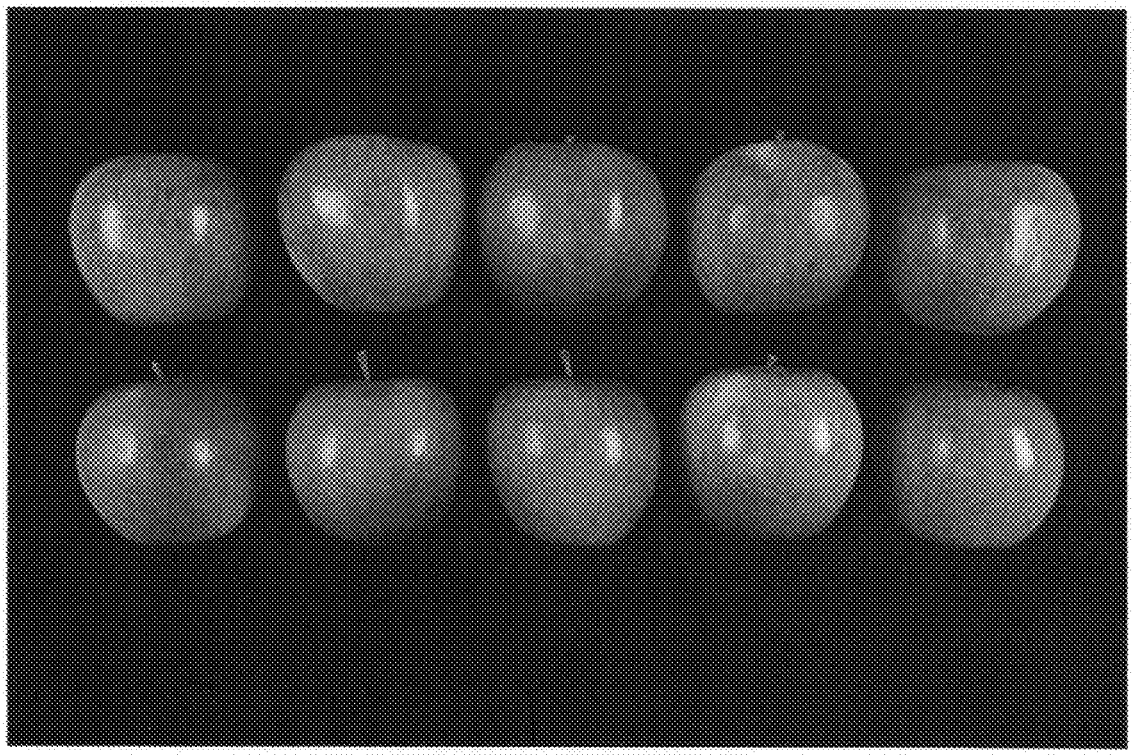
FIG. 2 shows typical fruit in profile of the variety 'Scilate'.
Figure 3:
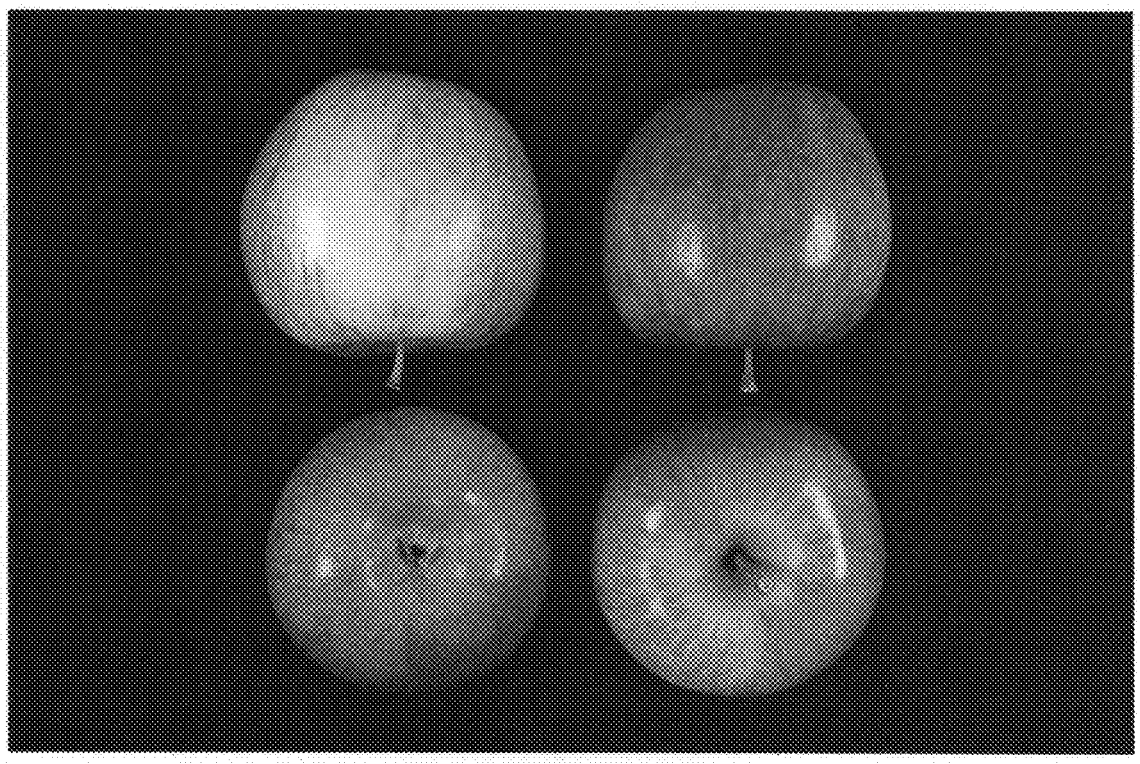
FIG. 3 shows typical stem end and calyx end views, and the exposed and shade sides of fruit of the variety 'Scilate'.
Figure 4:
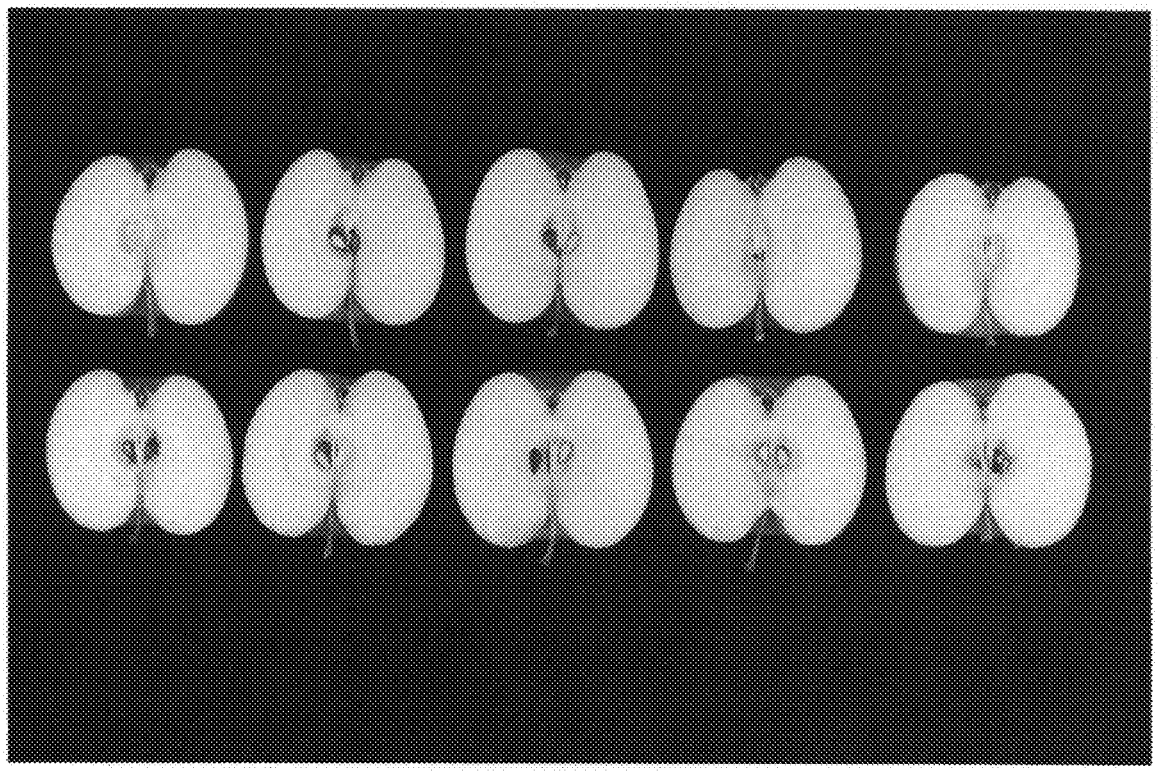
FIG. 4 shows typical fruit of the variety 'Scilate' longitudinal-section.
Figure 5:
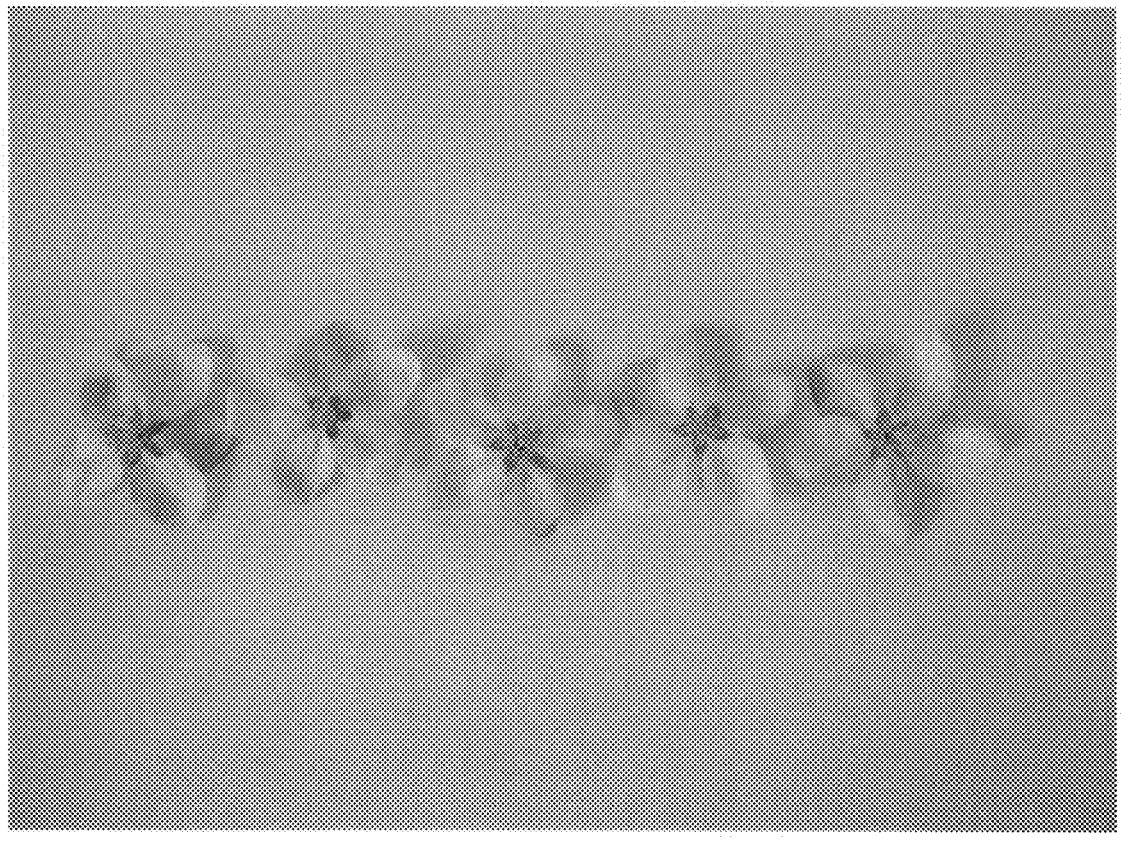
FIG. 5 shows flowers of the variety 'Scilate' from above.
Figure 6:
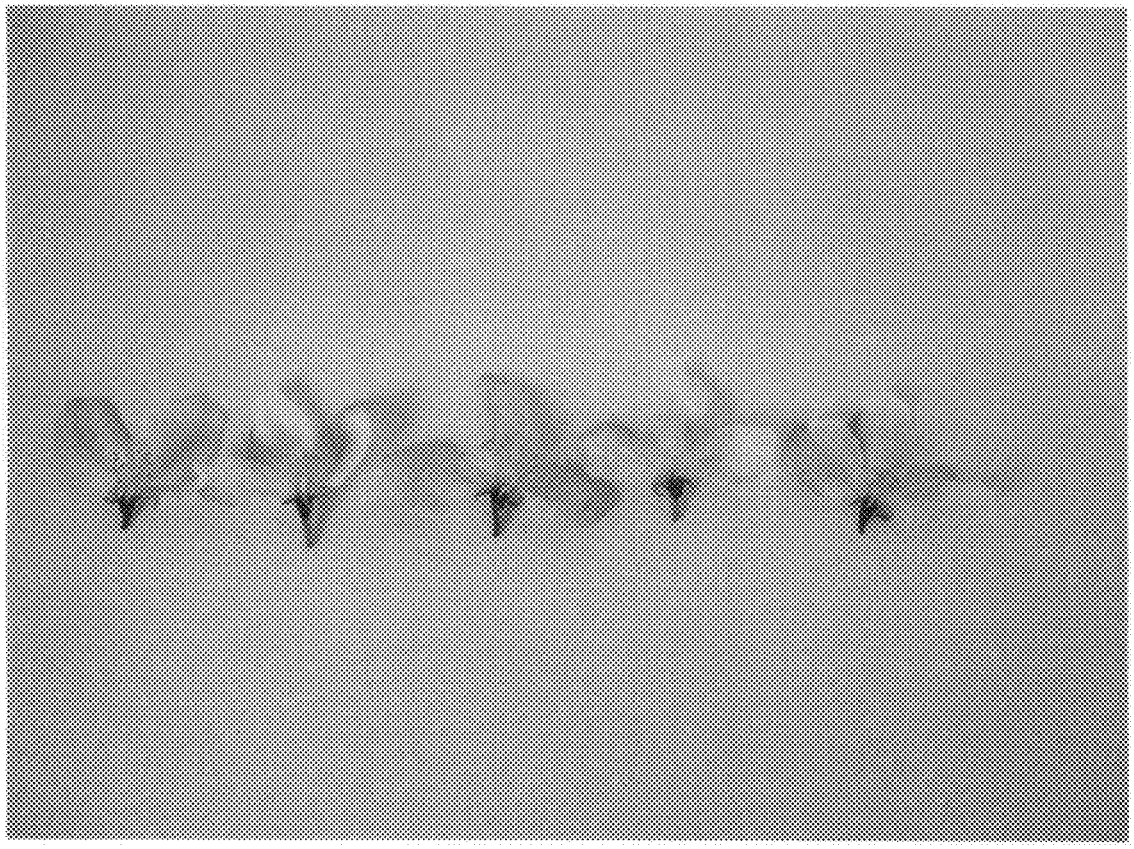
FIG. 6 shows flowers of the variety 'Scilate' in longitudinal section.
Figure 7:
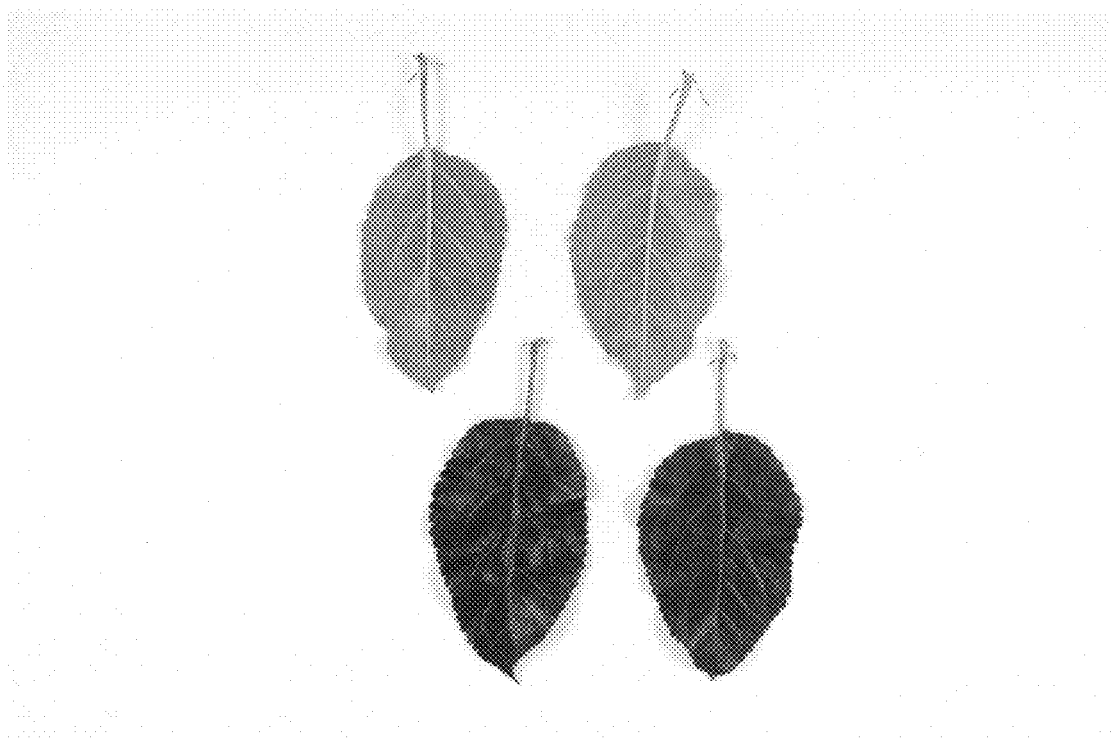
FIG. 7 shows typical leaves of the variety 'Scilate'.

The following is a detailed description of the new variety with colour terminology in accordance with The Royal Horticultural Society Colour Charts (R.H.S.C.C.) 2001 edition.

The specimens described were grown at Havelock North, Hawkes Bay, New Zealand. The observations were made in the 2004-2005 season on trees on MM. 106 rootstock that were four years old at the time, and managed under standard orchard practice.

Tree: Ramified with spreading habit; bearing on spurs and shoots; medium vigour. Average tree height 3.0 m and canopy diameter of 2.5 m measured at 1.0 m above the ground.

Trunk: Moderately rough; average diameter 47 mm at a height of 200 mm from the graft union; bark is grey-green R.H.S.C.C. 197B.

Branches: Angle of branching from the trunk is fairly flat, typically between 0° to 30° above the horizontal; moderate branching; moderately rough; pubescence absent; average number of 6 spurs per $cm^2$; colour grey-green R.H.S.C.C. 197B.

One year old shoot: Thickness 5mm; length 351 mm; internode length 29 mm; brown R.H.S.C.C. 166A.

Lenticels: Oval shape, size 1.0×0.5 mm; approximately 8 per $cm^2$; colour grey-white R.H.S.C.C. 156C.

Leaves: Length 89 mm; width 48 mm; outward attitude in relation to shoot; upfolded in cross section; crenate indentations; medium glossiness on upper surface; weak pubescence on lower surface; colour of mature leaf blade is green, upper surface R.H.S.C.C. 147A, lower surface R.H.S.C.C. 148B; colour of veins is green, upper surface R.H.S.C.C. 148B, lower surface R.H.S.C.C. 148D changing to red R.H.S.C.C. 182A from about mid way along the leaf towards the petiole; colour of immature leaf blade is green, upper surface R.H.S.C.C. 137B, lower surface R.H.S.C.C. 146B; elongate stipules, length 10 mm long, width 2 mm, petiole length 30 mm, thickness 2 mm; bud break is in early September in New Zealand.

Flower buds: Balloon stage length 16 mm, width 13 mm, colour pink R.H.S.C.C. N57D; initial bud colour is pink R.H.S.C.C. 63B.

Flowers: Medium blooming period, starting about 5 October for 2 weeks (Hawkes Bay, New Zealand); five petals, margins overlapping; colour pink R.H.S.C.C. 55B fading to white; flower diameter 45 mm; petal length 22 mm; petal width 16 mm; five pointed sepals, length 7 mm, width 3 mm, colour green R.H.S.C.C. 144D with red-orange tips R.H.S.C.C. 34A; many stamens with white filaments R.H.S.C.C. 155B, length 2.5-5 mm long and yellow anthers R.H.S.C.C. 11C, size 1.5×0.5mm; pollen colour yellow R.H.S.C.C. 4A; pistil—stigma length 8-9 mm, colour green R.H.S.C.C. 145B; five styles fused at base; fragrance mild.

Fruit: Harvest period is from about 19 April and continues for around three weeks in Hawkes Bay, New Zealand, Size: Medium; average width 81 mm; average height 69 mm; average weight 227 g.

Shape: Globose conical; symmetrical; ribbing weak; medium crowning at calyx end.

Stem cavity: Average depth 17 mm; average width 37 mm.

Eye basin: Average depth 13 mm; average width 30 mm; average diameter of eye 10 mm; aperture of eye partly open; sinus open.

Stem: Average length 22 mm; average thickness 2 mm.

Sepals: Average length 5 mm; touching; pointed, colour green R.H.S.C.C. 147C.

Skin: Medium thickness; smooth; bloom absent; greasiness absent at harvest; background colour yellow R.H.S.C.C. 11A; size of lenticels medium; small amounts of russet may be present on the cheek, in the stem basin and eye cavity and on the lenticels; overcolour covers about 70% of skin surface; red stripes R.H.S.C.C. 46A over a solid red flush R.H.S.C.C. 42B.

Flesh: Firmness of 10.8 kgf at harvest, crisp and juicy; cream coloured R.H.S.C.C. 13D; texture medium; sweet flavour with a hint of acidity, soluble solids 14%.

Locules: Five locules containing 1-2 seeds; aperture partly open; average length 17 mm; average width 10 mm.

Seeds: Average number per fruit 7; average length 10 mm; average width 5.2 mm; average thickness 3 mm; colour brown R.H.S.C.C. 165A.

Use: Dessert.

Keeping quality: Stores well in air cool storage (0±0.5° C.) for at least 3 months. Post storage firmness 10.1 kgf, soluble solids 16.5%. Fruit remains in a good condition for at least 14 days at 20° C.

Production: Late season; regular cropping; good fruit size and yield.

Disease susceptibility: no known resistances to pests and diseases.

Management: Prune in winter to open up the canopy to light; thin the crop in late spring. It is advisable to support young trees with posts and wires to prevent breakages. As this variety is prone to russet, spray applications should be applied in conditions which do not induce russet.

The specific pollination requirements have not been determined for the new variety. However, observations indicate that apple tree productivity is increased where cross-pollination readily occurs.

The ploidy of the candidate variety is not readily available. However, it is likely to be diploid consistent with the parent varieties. No indication of the variety being self-fertile, or partially self-fertile, has been observed and facilitation of cross-pollination is recommended to ensure a high level of productivity. The flowering period for the new variety is consistent with a number of mainstream varieties. Other varieties flowering in this period that could be considered as useful for cross-pollination of the new variety could include 'Royal Gala' (U.S. Plant Pat. No. 4,121), 'Red Delicious' (not patented), and 'Granny Smith' (not patented).

What is claimed is:

1. A new and distinct variety of apple tree substantially as herein described and illustrated.

* * * * *